United States Patent [19]

Johnston et al.

[11] Patent Number: 5,576,283

[45] Date of Patent: Nov. 19, 1996

[54] LIQUID DETERGENTS CONTAINING A PEPTIDE ALDEHYDE

[75] Inventors: James P. Johnston, Overijse; Regine Labeque, Neder-over-Heembeek, both of Belgium; Pierre M. A. Lenoir, Zurich, Switzerland; Christiaan A. J. K. Thoen, Haasdonk, Belgium; John M. McIver, Cincinnati, Ohio

[73] Assignee: The Procter & Gamble Company, Cincinnati, Ohio

[21] Appl. No.: 381,892

[22] PCT Filed: Jul. 28, 1993

[86] PCT No.: PCT/US93/07086

§ 371 Date: Feb. 8, 1995

§ 102(e) Date: Feb. 8, 1995

[87] PCT Pub. No.: WO94/04651

PCT Pub. Date: Mar. 3, 1994

[30] Foreign Application Priority Data

Aug. 14, 1992 [EP] European Pat. Off. .......... 92870121.8

[51] Int. Cl.$^6$ .................................................. C11D 3/386
[52] U.S. Cl. ........................ 510/321; 510/393; 510/530
[58] Field of Search ................ 252/174.12, DIG. 12, 252/DIG. 14, 174; 435/188

[56] References Cited

U.S. PATENT DOCUMENTS

| | | | |
|---|---|---|---|
| 4,045,552 | 8/1977 | Kutzbach et al. ...................... 424/94 |
| 4,305,837 | 12/1981 | Kaminsky et al. ................ 252/174.12 |
| 4,318,818 | 3/1982 | Letton et al. ...................... 252/174.12 |
| 4,399,065 | 8/1983 | Bajusz et al. ........................ 260/112.5 |
| 4,435,307 | 3/1984 | Barbesgaard ...................... 252/174.12 |
| 4,478,745 | 10/1984 | Bajusz et al. ....................... 260/112.5 |
| 4,537,773 | 8/1985 | Shenvi .................................. 514/63 |
| 4,562,292 | 12/1985 | Hammock et al. ...................... 568/43 |
| 4,566,985 | 1/1986 | Bruno et al. ...................... 252/174.12 |
| 4,593,018 | 6/1986 | Austen et al. ........................... 514/16 |
| 4,842,758 | 6/1989 | Crutzen ..................................... 252/8.7 |
| 4,908,150 | 3/1990 | Hessel et al. ...................... 252/174.12 |
| 5,015,627 | 5/1991 | Lindsey et al. .......................... 514/12 |
| 5,039,446 | 8/1991 | Estell et al. ....................... 252/174.12 |
| 5,106,948 | 4/1992 | Kinder et al. ........................... 530/331 |
| 5,178,789 | 1/1993 | Estell ................................ 252/174.12 |
| 5,283,293 | 2/1994 | Webb ................................. 525/332.2 |
| 5,284,829 | 2/1994 | McKerrow et al. ...................... 514/18 |
| 5,288,707 | 2/1994 | Metternich ............................... 514/19 |
| 5,306,444 | 4/1994 | Kitamura et al. ..................... 252/546 |

FOREIGN PATENT DOCUMENTS

| | | | |
|---|---|---|---|
| 293881 | 12/1988 | European Pat. Off. .......... C07K 5/00 |
| 381262 | 8/1990 | European Pat. Off. ........ C11D 3/386 |
| 1-296987 | 11/1989 | Japan ............................... C12N 9/54 |
| WO92/03529 | 3/1992 | WIPO ........................... C11D 3/386 |
| WO92/05239 | 4/1992 | WIPO ........................... C11D 3/386 |
| WO92/19707 | 11/1992 | WIPO ........................... C11D 3/386 |
| WO93/13125 | 7/1993 | WIPO ........................... C07K 3/00 |

OTHER PUBLICATIONS

Bender, Kinetics of subtilisin and thiolsubtilisin, Molecular and Cellular Biochemistry, pp. 1–32, (1983).

Philipp, M., "Kinetics of Subtilisin and Thiolsubtilisin", Molecular and Cellular Biochemsitry 51 (1983), pp. 5–32.

Nagy, I., "Tripeptide Aldehyde Protease Inhibitors May Depress in Vitro Prolactin and growth Hormone Release", Endocrinology (1985), vol. 116, No. 4, pp. 1426–1432.

*Primary Examiner*—Douglas J. McGinty
*Assistant Examiner*—Kery A. Fries
*Attorney, Agent, or Firm*—K. W. Zerby; J. J. Yetter; T. D. Reed

[57] ABSTRACT

Aqueous liquid detergent compositions are described which comprise a proteolytic enzyme wherein the proteolytic activity is reversibly inhibited by a peptide aldehyde.

6 Claims, No Drawings

LIQUID DETERGENTS CONTAINING A PEPTIDE ALDEHYDE

FIELD OF THE INVENTION

This invention relates to liquid detergent compositions containing enzymes. More specifically, this invention pertains to liquid detergent compositions containing a detersive surfactant, a proteolytic enzyme, and a peptide aldehyde.

BACKGROUND OF THE INVENTION

Protease-containing liquid aqueous detergents are well-known, especially in the context of laundry washing. A commonly encountered problem in such protease-containing liquid aqueous detergents is the degradation phenomenon by the proteolytic enzyme of second enzymes in the composition, such as lipase, amylase and cellulase, or on the protease itself.

As a result, the stability of the second enzyme or the protease itself in the detergent composition is affected and the detergent composition consequently performs less well.

In response to this problem, it has been proposed to use various protease inhibitors or stabilizers. For instance, U.S. Pat. No. 4,566,985 proposes to use benzamidine hydrochloride, EP 376 705 proposes to use lower aliphatic alcohols or carboxylic acids, EP 381 262 proposes to use a mixture of a polyol and a boron compound, and co-pending application EP 91870072.5 proposes to use aromatic borate esters.

It is thus an object of the present invention to provide other reversible protease inhibitors which are effective and suitable for use in an aqueous liquid detergent composition.

In response to this object, the present invention proposes to use peptide aldehydes as reversible protease inhibitors in aqueous liquid detergent compositions.

A particular advantage of the present invention is that peptide aldehydes need only to be used at very low levels in the liquid detergent compositions herein. Thus several parts of materials are made available for other ingredients. This is particularly critical in the formulation of concentrated liquid detergent compositions which are encompassed by the present invention.

Because the peptide aldehydes according to the present invention are so efficient in inhibiting proteases, another advantage of the present invention is that even enzymes which are highly sensitive to proteolytic degradation can now be incorporated in liquid detergent compositions comprising a protease.

The use of peptide derivatives for the inhibition of proteins appears to have been disclosed so far only in therapeutic applications. For instance, EP 293 881 discloses the use of peptide boronic acids as inhibitors of trypsin-like serine proteases. EP 185 390 and U.S. Pat. No. 4,399,065 disclose the use of certain peptide aldehydes derivatives for the inhibition of blood coagulation. J 90029670 discloses the use of optically active alpha amino aldehydes for the inhibition of enzymes in general. See also "Inhibition of Thrombin and Trypsin by Tripeptide Aldehydes", *Int. J. Peptide Protein Res.*, Vol 12 (1978), pp. 217–221; Gaal, Bacsy & Rappay, and "Tripeptide Aldehyde Protease Inhibitors May Depress in Vitro Prolactin and Growth Hormone Release" *Endocrinology*, Vol. 116. No. 4 (1985), pp. 1426–1432; Rappay, Makara, Bajusz & Nagy. Certain peptide aldehydes have also been disclosed in EP-A-473 502 for inhibiting protease-mediated skin irritation.

SUMMARY OF THE INVENTION

The present invention is a liquid aqueous detergent composition comprising:
from 1% to 80% of a detersive surfactant,
from 0.0001% to 1.0% of an active proteolytic enzyme or mixtures thereof,
characterized in that it further comprises from 0.00001% to 5% of a peptide aldehyde comprising from 2 to 50 amino acids, or a mixture thereof.

DETAILED DESCRIPTION OF THE INVENTION

The liquid aqueous detergent compositions according to the present invention comprise three essential ingredients: (A) a peptide aldehyde or a mixture thereof, (B) a proteolytic enzyme or a mixture thereof, and (C) a detersive surfactant. The compositions according to the present invention preferably further comprise (D) a detergent-compatible second enzyme or a mixture thereof, and may further comprise (E) optional ingredients.

A. Peptide aldehydes

The detergent compositions according to the present invention comprise, as a first essential ingredient, a peptide aldehyde comprising from 2 to 50 amino acids, or mixtures thereof. As used herein, the term peptide aldehydes refers to compounds comprising a peptidic chain wherein the C-terminal end of said chain is converted from a carboxylic group to an aldehyde group. Peptide aldehydes are known per se and have been described, as well as processes for their manufacture, for instance in U.S. Pat. No. 5,015,627, EP 185 930 and DE 32 00 812. Preferred peptide aldehydes for use herein comprise from 2 to 6 amino acids, most preferably 3 to 4.

While not wanting to be bound by theory it is believed that the peptide aldehydes according to the present invention bind to the proteolytic enzyme in the liquid detergent composition, thereby inhibiting said proteolytic enzyme. Upon dilution in water, the proteolytic activity is restored by dissociation of the proteolytic enzyme/peptide aldehyde complex.

The N-terminal end of said peptidic chain in the peptide aldehydes according to the present invention may be protected by appropriate protecting groups which are known to the man skilled in the art. However, in a highly preferred embodiment of the present invention, the N-terminal end of said peptidic chain is protected by a methyl carbamate ($CH_3O$—(O)C—) or methyl urea ($CH_3N$—(O)C—) group. Indeed, it has been found that peptide aldehydes according to the present invention which have methyl carbamate or methyl urea as N-terminal protecting groups are particularly stable, in that the efficiency of said protected peptide aldehydes in inhibiting proteolytic activity is better sustained throughout time, compared to unprotected or otherwise protected peptide aldehydes.

A particular advantage of the present invention is that it can be tailored to each individual situation. Specifically, depending on the protease which is used in a given detergent composition, peptide aldehydes can be selected which are more effective than others in reversibly inhibiting said protease. Existing proteases can be divided into trypsin, subtilisin, chymotrypsin and elastase -type proteases. For trypsin-type proteases, suitable peptide aldehydes will include Lys-Ala-LysH, Ile-Phe-LysH, Phe-Pro-ArgH and Phe Val-ArgH. For subtilisin-type proteases, suitable peptide aldehydes will include Lys-Ala-AlaH, Ala-Ala-ProH, Gly- Ala-LeuH, Gly-Ala-PheH, Phe-Gly-Ala-PheH and Phe-Gly-Ala-LeuH. For chymotrypsin-type proteases, suitable peptide aldehydes will include Leu-Leu-PheH, Ala-Ala-PheH and Leu-Leu-TyrH. For Elastase-type proteases, suitable peptide aldehydes will include Val-Pro-ValH and Ala-Val-LeuH.

The preferred proteases for use in the detergent compositions which are described in part B) hereinafter are subtilisin-type proteases. Thus, the preferred petide aldehydes for use herein are Lys-Ala-Ala-H, Ala-Ala-ProH, Gly-Ala-LeuH, Gly-Ala-PheH, Phe-Gly-Ala-PheH and Phe-Gly-Ala-LeuH. Particularly preferred for use herein are Gly-Ala-LeuH, Gly-Ala-PheH, Phe-Gly-Ala-PheH and Phe-Gly-Ala-LeuH, i.e. the N-terminal end of the peptides is, respectively, Gly, Gly, Phe and Phe, and the C-terminal end of the peptides is respectively Leu, Phe, Phe and Leu. The carboxylic group of these C-terminal amino acids is converted to an aldehyde group.

All peptide aldehydes listed herein will of course be preferably used in their methyl carbamate or methyl urea N-terminal protected form. In the examples hereinafter methods are disclosed to synthesize $CH_3O$—(O) C-Phe-Gly-Ala-LeuH, $CH_3O$—(O) C-Phe-Gly-Ala-PheH, $CH_3N$—(O) C-Phe-Gly-Ala-LeuH and $CH_3N$—(O) C-Phe-Gly-Ala-PheH.

The compositions according to the present invention comprise from 0.00001% to 5% by weight of the total composition of a peptide aldehyde or mixtures thereof, preferably 0.0001% to 1%, most preferably from 0.0005% to 0.2%.

B. Proteolytic Enzyme

A second essential ingredient in the present liquid detergent compositions is from about 0.0001 to 1.0, preferably about 0.0005 to 0.2, most preferably about 0.002 to 0.1, weight % of active proteolytic enzyme. Mixtures of proteolytic enzyme are also included. The proteolytic enzyme can be of animal, vegetable or microorganism (preferred) origin. Preferred for use herein are subtilisin-type proteolytic enzymes. Particularly preferred is bacterial serine proteolytic enzyme obtained from *Bacillus subtilis* and/or *Bacillus licheniformis*.

Suitable proteolytic enzymes include Novo Industri A/S Alcalase® (preferred), Esperase®, Savinase® (Copenhagen, Denmark), Gist-brocades' Maxatase®, Maxacal®, and Maxapem 15® (protein engineered Maxacal®) (Delft, Netherlands), and subtilisin BPN and BPN'(preferred), which are commercially available. Preferred proteolytic enzymes are also modified bacterial serine proteases, such as those made by Genencor International, Inc.(San Francisco, Calif.) which are described in European Patent Application Serial Number 87303761.8, filed Apr. 28, 1987 (particularly pages 17, 24 and 98), and which is called herein "Protease B", and 199,404, Venegas, published Oct. 29, 1986, which refers to a modified bacterial serine proteolytic enzyme (Genencor International) which is called "Protease A" herein (same as BPN'). Preferred proteolytic enzymes, then, are selected from the group consisting of Alcalase® (Novo Industri A/S), BPN', Protease A and Protease B (Genencor), and mixtures thereof. Protease B is most preferred.

C. Detersive Surfactant

From about 1 to 80, preferably about 5 to 50, most preferably about 10 to 30, weight % of detersive surfactant is the third essential ingredient in the present invention. The detersive surfactant can be selected from the group consisting of anionics, nonionics, cationics, ampholytics, zwitterionics, and mixtures thereof. Although the compositions according to the present invention are preferably used in the context of laundry cleaning, said compositions according to the present invention can be used in other different cleaning applications including hard surface cleaning, or dishwashing. The particular surfactants used can therefore vary widely depending upon the particular end-use envisioned.

The benefits of the present invention are especially pronounced in compositions containing ingredients that are harsh to enzymes such as certain detergency builders and surfactants. These, in general, include (but are not limited to anionic surfactants such as alkyl ether sulfate linear alkyl benzene sulfonate, alkyl sulfate, etc. Suitable surfactants are described below.

Anionic Surfactants

One type of anionic surfactant which can be utilized encompasses alkyl ester sulfonates. These are desirable because they can be made with renewable, non-petroleum resources. Preparation of the alkyl ester sulfonate surfactant component can be effected according to known methods disclosed in the technical literature. For instance, linear esters of $C_8$–$C_{20}$ carboxylic acids can be sulfonated with gaseous $SO_3$ according to "The Journal of the American Oil Chemists Society," 52 (1975), pp. 323–329. Suitable starting materials would include natural fatty substances as derived from tallow, palm, and coconut oils, etc.

The preferred alkyl ester sulfonate surfactant, especially for laundry applications, comprises alkyl ester sulfonate surfactants of the structural formula:

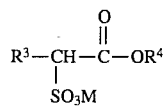

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a soluble salt-forming cation. Suitable salts include metal salts such as sodium, potassium, and lithium salts, and substituted or unsubstituted ammonium salts, such as methyl-, dimethyl, -trimethyl, and quaternary ammonium cations, e.g. tetramethyl-ammonium and dimethyl piperdinium, and cations derived from alkanolamines, e.g. monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{14}$–$C_{16}$ alkyl.

Alkyl sulfate surfactants are another type of anionic surfactant of importance for use herein. In addition to providing excellent overall cleaning ability when used in combination with polyhydroxy fatty acid amides (see below), including good grease/oil cleaning over a wide range of temperatures, wash concentrations, and wash times, dissolution of alkyl sulfates can be obtained, as well as improved formulability in liquid detergent formulations are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethylammonium and quaternary ammonium cations, such as tetramethyl-ammonium, dimethyl piperidinium and cations derived from alkanolamines, e.g. monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium.

Other Anionic Surfactants

Other anionic surfactants useful for detersive purposes can also be included in the compositions hereof. These can include salts (including, for example, sodium, potassium, ammonium, and substituted ammonia salts such as mono-, di- and triethanolamine salts) of soap, $C_9$–$C_{20}$ linear alkylbenzenesulphonates, $C_8$–$C_{22}$ primary or secondary alkanesulphonates, $C_8$–$C_{24}$ olefinsulphonates, sulphonated polycarboxylic acids prepared by sulphonation of the pyrolyzed product of alkaline earth metal citrates, e.g., as described in British patent specification No. 1,082,179, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—$M^+$ wherein R is a $C_8$–$C_{22}$ alkyl, k is an integer from 0 to 10, and M is a soluble salt-forming cation, and fatty acids esterified with isethionic acid and neutralized with sodium hydroxide. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through column 29, line 23 (herein incorporated by reference).

Nonionic Detergent Surfactants

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal® CO-630, marketed by the GAF Corporation; and Triton® X-45, X-114, X-100, and X-102, all marketed by the Rohm & Haas Company. These compounds are commonly referred to as alkyl phenol alkoxylates, (e.g., alkyl phenol ethoxylates).

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include Tergitol® 15-S-9 (the condensation product of $C_{11}$–$C_{15}$ linear secondary alcohol with 9 moles ethylene oxide), Tergitol® 24-L-6 NMW (the condensation product of $C_{12}$–$C_{14}$ primary alcohol with 6 moles ethylene oxide with a narrow molecular weight distribution), both marketed by Union Carbide Corporation; Neodol® 45-9 (the condensation product of $C_{14}$–$C_{15}$ linear alcohol with 9 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 45-4 (the condensation product of $C_{14}$–$C_{15}$ linear alcohol with 4 moles of ethylene oxide), marketed by Shell Chemical Company, and Kyro® EOB (the condensation product of $C_{13}$–$C_{15}$ alcohol with 9 moles ethylene oxide), marketed by The Procter & Gamble Company. This category of nonionic surfactant is referred to generally as "alkyl ethoxylates."

3. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic® surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic® compounds, marketed by BASF.

5. Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula $$R^3(OR^4)_xN(R^5)_2 \overset{O}{\uparrow}$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1, to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units.

Optionally, and less desirably, there can be a polyalkylene-oxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkyleneoxide moieties. Suitable alkyl polysaccharides are octyl, nonyl, decyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexa-glucosides.

The preferred alkylpolyglycosides have the formula $$R^2O(C_nH_{2n}O)_t(glycosyl)_x$$

wherein $R^2$ is selected from the group consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

7. Fatty acid amide surfactants having the formula:

$$R^6 - \overset{O}{\overset{\|}{C}} - N(R^7)_2$$

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and $-(C_2H_4O)_xH$ where x varies from about 1 to about 3.

Preferred amides are $C_8$–$C_{20}$ ammonia amides, monoethanolamides, diethanolamides, and isopropanolamides.

Cationic Surfactants

Cationic detersive surfactants can also be included in detergent compositions of the present invention. Cationic surfactants include the ammonium surfactants such as alkyldimethylammonium halogenides, and those surfactants having the formula:

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain, each $R^3$ is selected from the group consisting of $-CH_2CH_2-$, $-CH_2CH(CH_3)-$, $-CH_2CH(CH_2OH)-$, $-CH_2CH_2CH_2-$, and mixtures thereof; each $R^4$ is selected from the group consisting of $C_1$–$C_4$ alkyl, $C_1$–$C_4$ hydroxyalkyl, benzyl, ring structures formed by joining the two $R^4$ groups, $-CH_2CHOH-CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Other cationic surfactants useful herein are also described in U.S. Pat. No. 4,228,044, Cambre, issued Oct. 14, 1980, incorporated herein by reference.

Other Surfactants

Ampholytic surfactants can be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight chain or branched. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 to Laughlin et al., issued Dec. 30, 1975 at column 19, lines 18–35 (herein incorporated by reference) for examples of ampholytic surfactants.

Zwitterionic surfactants can also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48 (herein incorporated by reference) for examples of zwitterionic surfactants.

Ampholytic and zwitterionic surfactants are generally used in combination with one or more anionic and/or nonionic surfactants.

Polyhydroxy Fatty Acid Amide Surfactants

The liquid detergent compositions hereof may also contain an "enzyme performance-enhancing amount" of polyhydroxy fatty acid amide surfactant. By "enzyme-enhancing" is meant that the formulator of the composition can select an amount of polyhydroxy fatty acid amide to be incorporated into the compositions that will improve enzyme cleaning performance of the detergent composition. In general, for conventional levels of enzyme, the incorporation of about 1%, by weight, polyhydroxy fatty acid amide will enhance enzyme performance.

The detergent compositions hereof will typically comprise at least about 1% weight basis, polyhydroxy fatty acid amide surfactant and preferably at least from about 3% to about 50%, most preferably from about 3% to 30%, of the polyhydroxy fatty acid amide.

The polyhydroxy fatty acid amide surfactant component comprises compounds of the structural formula:

$$R^2 - \underset{\underset{O}{\|}}{C} - \underset{\underset{R^1}{|}}{N} - Z \quad (I)$$

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, and alkoxylated derivatives thereof, where n is an integer from 3 to 5, inclusive, and R' is H or a cyclic or aliphatic monosaccharide. Most preferred are glycityls wherein n is 4, particularly —$CH_2$—$(CHOH)_4$—$CH_2OH$.

In Formula (I), R' can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

D. Second Enzyme

Preferred compositions herein further comprise a performance-enhancing amount of a detergent-compatible second enzyme. By "detergent-compatible" is meant compatibility with the other ingredients of a liquid detergent composition, such as detersive surfactant and detergency builder. These second enzymes are preferably selected from the group consisting of lipase, amylase, cellulase, and mixtures thereof. The term "second enzyme" excludes the proteolytic enzymes discussed above, so each composition contains at least two kinds of enzyme, including at least one proteolytic enzyme. The amount of second enzyme used in the composition varies according to the type of enzyme. In general, from about 0.0001 to 0.3, more preferably 0.001 to 0.1, weight % of these second enzymes are preferably used. Mixtures of the same class of enzymes (e.g. lipase) or two or more classes (e.g. cellulase and lipase) may be used. Purified or non-purified forms of the enzyme may be used.

Any lipolytic enzyme suitable for use in a liquid detergent composition can be used in these compositions. Suitable lipase enzymes for use herein include those of bacterial and fungal origin.

Suitable bacterial lipases include those produced by microorganisms of the Pseudomonas groups, such as *Pseudomonas stutzeri* ATCC 19.154, as disclosed in British Patent 1,372,034, incorporated herein by reference. Suitable lipases include those which show a positive immunological cross-reaction with the antibody of the lipase produced by the microorganism *Pseudomonas fluorescens* IAM 1057. This lipase and a method for its purification have been described in Japanese Patent Application 53-20487, laid open on Feb. 24, 1978. This lipase is available from Amano Pharmaceutical Co. Ltd., Nagoya, Japan, under the trade name Lipase P "Amano," hereinafter referred to as "Amano-P." Such lipases should show a positive immunological cross-reaction with the Amano-P antibody, using the standard and well-known immunodiffusion procedure according to Ouchterlony (Acta. Med. Scan., 133, pages 76–79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Pseudomonas nitroreducens* var. *lipolyticum* FERM P 1338 (available under the trade name Amano-CES), lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*.

Suitable fungal lipases include those producible by *Humicola lanuginosa* and *Thermomyces lanuginosus*. Most preferred is lipase obtained by cloning the gene from *Humicola lanuginosa* and expressing the gene in *Aspergillus oryzae* as described in European Patent Application 0 258 068 (Novo Industri A/S), commercially available from Novo Nordisk A/S under the trade name Lipolase®.

From about 10 to 18,000, preferably about 60 to 6,000, lipase units per gram (LU/g) of lipase can be used in these compositions. A lipase unit is that amount of lipase which produces 1 μmol of titratable fatty acid per minute in a pH star, where pH is 9.0, temperature is 30° C., substrate is an emulsion of 3.3 wt % of olive oil and 3.3% gum arabic, in the presence of 13 μmol/l $Ca^{++}$ and 20 μmol/l NaCl in 5 μmol/l Tris-buffer.

Any cellulase suitable for use in a liquid detergent composition can be used in these compositions. Suitable cellulase enzymes for use herein include those from bacterial and fungal origins. Preferably, they will have a pH optimum of between 5 and 9.5. From about 0.0001 to 0.1 weight % cellulase can be used.

Suitable cellulases are disclosed in U.S. Pat. No. 4,435,307, Barbesgaard et al., issued Mar. 6, 1984, incorporated herein by reference, which discloses fungal cellulase produced from *Humicola insolens*. Suitable cellulases are also disclosed in GB-A-2.075.028, GB-A-2.095.275 and DE-OS-2.247.832.

Examples of such cellulases are cellulases produced by a strain of *Humicola insolens* (*Humicola grisea* var. *thermoidea*), particularly the Humicola strain DSM 1800, and cellulases produced by a fungus of Bacillus N or a cellulase 212-producing fungus belonging to the genus Aeromonas, and cellulase extracted from the hepatopancreas of a marine mollusc (Dolabella Auricula Solander).

Any amylase suitable for use in a liquid detergent composition can be used in these compositions. Amylases include, for example, amylases obtained from a special strain of *B. licheniformis*, described in more detail in British Patent Specification No. 1,296,839 (Novo). Amylolytic proteins include, for example, Rapidase®, International Bio-Synthetics, Inc. and Termamyl® Novo Industries.

From about 0.0001% to 0.55, preferably 0.0005 to 0.1, wt. % amylase can be used.

E. Optional Ingredients

Detergent builders can optionally be included in the compositions herein. From 0 to about 50 weight % deter-gency builder can be used herein. Inorganic as well as organic builders can be used. When present, the compositions will typically comprise at least about 1% builder. Liquid formulations preferably comprise from about 3% to 30%, more preferably about 5 to 20%, by weight, of detergent builder.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Borate builders, as well as builders containing borate-forming materials that can produce borate under detergent storage or wash conditions (hereinafter, collectively "borate builders"), can also be used. Preferably, non-borate builders are used in the compositions of the invention intended for use at wash conditions less than about 50° C., especially less than about 40° C.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck, incorporated herein by reference. However, other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates, including sodium carbonate and sesquicarbonate and mixtures thereof with ultra-fine calcium carbonate as disclosed in German Patent Application No. 2,321,001 published on Nov. 15, 1973, the disclosure of which is incorporated herein by reference.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

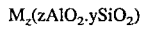

$$M_z(zAlO_2 \cdot ySiO_2)$$

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate. Preferred alumino-silicates are zeolite builders which have the formula:

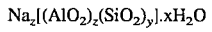

$$Na_z[(AlO_2)_z(SiO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al., issued Oct. 12, 1976, incorporated herein by reference. Preferred synthetic crystalline aluminosilicate ion exchange materials useful herein are available under the designations Zoolite A, Zoolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zoolite A. Preferably, the aluminosilicate has a particle size of about 0.1–10 microns in diameter.

Specific examples of polyphosphates are the alkali metal tripolyphosphates, sodium, potassium and ammonium pyrophosphate, sodium and potassium and ammonium pyrophosphate, sodium and potassium orthophosphate, sodium polymeta phosphate in which the degree of polymerization ranges from about 6 to about 21, and salts of phytic acid.

Examples of phosphonate builder salts are the water-soluble salts of ethane 1-hydroxy-1, 1-diphosphonate particularly the sodium and potassium salts, the water-soluble salts of methylene diphosphonic acid e.g. the trisodium and tripotassium salts and the water-soluble salts of substituted methylene diphosphonic acids, such as the trisodium and tripotassium ethylidene, isopyropylidene benzylmethylidene and halo methylidene phosphonates. Phosphonate builder salts of the aforementioned types are disclosed in U.S. Pat. Nos. 3,159,581 and 3,213,030 issued Dec. 1, 1964 and Oct. 19, 1965, to Diehl; U.S. Pat. No. 3,422,021 issued Jan. 14, 1969, to Roy; and U.S. Pat. Nos. 3,400,148 and 3,422,137 issued Sep. 3, 1968, and Jan. 14, 1969 to Quimby, said disclosures being incorporated herein by reference.

Organic detergent builders preferred for the purposes of the present invention include a wide variety of polycarboxylate compounds. As used herein, "polycarboxylate" refers to compounds having a plurality of carboxylate groups, preferably at least 3 carboxylates.

Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et el., U.S. Pat. No. 3,635,830, issued Jan. 18, 1972, both of which are incorporated herein by reference.

A specific type of ether polycarboxylates useful as builders in the present invention also include those having the general formula:

CH(A)(COOX)—CH(COOX)—O—CH(COOX)—CH(COOX)(B)

wherein A is H or OH; B is H or —O—CH(COOX)—CH$_2$(COOX); and X is H or a salt-forming cation. For example, if in the above general formula A and B are both H, then the compound is oxydissuccinic acid and its water-soluble salts. If A is OH and B is H, then the compound is tartrate monosuccinic acid (TMS) and its water-soluble salts. If A is H and B is —O—CH(COOX)—CH$_2$(COOX), then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. These builders are disclosed in U.S. Pat. No. 4,663,071, issued to Bush et al., on May 5, 1987.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

HO—[C(R)(COOM)—C(R)(COOM)—O]$_n$—H wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Still other ether polycarboxylates include copolymers of maleic anhydride with ethylene or vinyl methyl ether, 1, 3, 5-trihydroxy benzene-2, 4, 6-trisulphonic acid, and carboxymethyloxysuccinic acid.

Organic polycarboxylate builders also include the various alkali metal, ammonium and substituted ammonium salts of polyacetic acids. Examples include the sodium, potassium, lithium, ammonium and substituted ammonium salts of ethylenediamine tetraacetic acid, and nitrilotriacetic acid.

Also included are polycarboxylates such as mellitic acid, succinic acid, oxydisuccinic acid, polymaleic acid, benzene 1,3,5-tricarboxylic acid, and carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations, but can also be used in granular compositions.

Other carboxylate builders include the carboxylated carbohydrates disclosed in U.S. Pat. No. 3,723,322, Diehl, issued Mar. 28, 1973, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Useful succinic acid builders include the $C_5$–$C_{20}$ alkyl succinic acids and salts thereof. A particularly preferred compound of this type is dodecenylsuccinic acid. Alkyl succinic acids typically are of the general formula R—CH(COOH)CH$_2$(COOH) i.e., derivatives of succinic acid, wherein R is hydrocarbon, e.g., $C_{10}$–$C_{20}$ alkyl or alkenyl, preferably $C_{12}$–$C_{16}$ or wherein R may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Examples of useful builders also include sodium and potassium carboxymethyloxymalonate, carboxymethyloxysuccinate, cis-cyclo-hexanehexacarboxylate, cis-cyclopentane-tetracarboxylate, water-soluble polyacrylates (these polyacrylates having molecular weights to above about 2,000 can also be effectively utilized as dispersants), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Polycarboxylate builders are also disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid and methylenemalonic acid.

Other organic builders known in the art can also be used. For example, monocarboxylic acids, and soluble salts thereof, having long chain hydrocarbyls can be utilized. These would include materials generally referred to as "soaps." Chain lengths of $C_{10}$–$C_{20}$ are typically utilized. The hydrocarbyls can be saturated or unsaturated.

Other optional ingredients include soil release agents, chelating agents, clay soil removal/anti redeposition agents, polymeric dispersing agents, bleaches, brighteners, suds suppresors, solvents and aesthetic agents.

The detergent composition herein can be formulated as a variety of compositions, for instance as laundry detergents as well as hard surface cleaners or dishwashing compositions.

The compositions according to the present invention are further illustrated by the following examples.

EXAMPLES

Example A

The following compositions were made by listing the listed ingredients in the listed proportions. In the examples hereinafter, the peptide aldehydes which were used were:

Peptide aldehyde 1: $CH_3O$—(O)C-Phe-Gly-Ala-LeuH
Peptide aldehyde 2: $CH_3N$—(O)C-Phe-Gly-Ala-LeuH
Peptide aldehyde 3: $CH_3O$—(O)C-Phe-Gly-Ala-PheH
Peptide aldehyde 4: $CH_3N$—(O)C-Phe-Gly-Ala-PheH

| Compositions | 1 | 2 | 3 | 4 | 5 | 6 |
|---|---|---|---|---|---|---|
| Linear alkyl benzene sulfonic acid | 8.5 | 15 | 6.5 | 10 | 12.5 | 4 |
| Sodium $C_{12-15}$ alkyl sulfate | 1 | 2 | 1 | 2 | 0 | 0 |
| $C_{14-15}$ alkyl 2.5 times ethoxylated sulfate | 10 | 5 | 10.5 | 0 | 11 | 9 |
| $C_{12}$ glucose amide | 0 | 0 | 9 | 0 | 0 | 5 |
| $C_{12-15}$ alcohol 7 times ethoxylated | 3 | 10 | 4 | 7 | 2.5 | 0 |
| Fatty acid | 2 | 5 | 5 | 4 | 2 | 2 |
| Citric acid | 5 | 6 | 7 | 4 | 6 | 4 |
| $C_{12-14}$ alkenyl substituted succinic acid | 0 | 6 | 0 | 5 | 0 | 6 |
| Sodium Hydroxide | 2 | 6 | 2 | 4 | 1 | 1.5 |
| Ethanol | 2 | 1.5 | 2 | 4 | 2 | 1.5 |
| Monoethanolamine | 6 | 5 | 4 | 0 | 0 | 0 |
| 1,2-propane diol | 12 | 10 | 5 | 5 | 4 | 6 |
| Amylase (143 KNU/g) | 0 | 0 | 0.1 | 0 | 0 | 0.2 |

-continued

| Compositions | 1 | 2 | 3 | 4 | 5 | 6 |
|---|---|---|---|---|---|---|
| LipolaseR (100 KLU/g commercial solution) | 0.5 | 0.2 | 0.5 | 0.5 | 0.4 | 0 |
| Protease B (34 g/L Commercial solution) | 0.9 | 0 | 0.5 | 0 | 1.2 | 0 |
| SavinaseR (Commercial solution) | 0 | 0.3 | 0 | 0.4 | 0.2 | 0.3 |
| CarezymeR (Experimental sample) | 0.5 | 1 | 0.8 | 0 | 0.2 | 0.8 |
| Peptide aldehyde 1 | 0.009 | — | — | — | — | 0.0003 |
| Peptide aldehyde 2 | — | — | 0.001 | — | 0.008 | — |
| Peptide aldehyde 3 | — | 0.005 | — | — | — | — |
| Peptide aldehyde 4 | — | — | — | 0.0005 | — | — |
| Water and minors | Balance to 100% | | | | | |

Example B

Peptide aldehydes are synthesized according to Schemes A ($CH_3O$—(O)C-Phe-Gly-Ala-LeuH) and B ($CH_3N$—(O)C-Phe Gly Ale Leu). In Scheme A and B some of the intermediates are purchased from suppliers and in these instances it is noted within the scheme. Dess-Martin periodinane is synthesized according to the procedure of Martin, J. Org. Chem., 1983, 48, 4155.

Z-Gly-Ala-Leu-OMe (5)—To a solution of Z-Gly-Ala-OH (3) (20.0 g, 0.071M) and Leu-OMe.HCl (12.9 g, 0.071M) in 250 ml dichloromethane was added 21.9 ml (0.157M) triethylamine (TEA) dropwise over a period of 10 min. This addition was followed by the addition of 11.9 ml (0.078M) of diethylcyanophosphonate (DECP). The mixture was stirred overnight and the solvent removed. The residue was dissolved in ethyl acetate and washed with 1N HCl, saturated $NaHCO_3$, and brine. The solution was dried with $MgSO_4$, filtered and the solvent removed. Recovered 29.0 g of product that is homogeneous by TLC. $^{13}$C NMR ($CDCl_3$) 15.93, 18.60, 21.77, 22.69, 24.72, 40.80, 44.20, 48.70, 50.87, 52.13, 65.28, 66.84, 127.92, 128.00, 128.41, 136.36, 156.76, 169.31, 172.58, 173.24.

Moc-Phe-Gly-Ala-Leu-OMe (6)—Z-Gly-Ala-Leu-OMe (5) (29.0 g, 0.071M) was dissolved in 300 ml MeOH and 35 ml 4.0M HCl in dioxane. To this solvent mixture is added 5.8 g of 10% Pd/C portionwise. The slurry is degassed with an aspirator and $H_2$ introduced via balloon. The slurry is maintained under a positive pressure of $H_2$ and stirred overnight. The slurry is filtered through Celite and a sintered glass funnel and washed thoroughly with MeOH. The solvent is removed and the residue is triturated with ether. The slurry is filtered and the filter cake dried under vacuum. Recovered 20.2 g of an off-white powder. The crude product and Moc-Phe-OH (15.3 g, 0.068M) were dissolved in 500 ml $CH_2Cl_2$ and 29.9 ml TEA (0.143M) added dropwise followed by the dropwise addition of 11.7 ml (0.072M) of DECP. The mixture was stirred overnight and the solvent was removed. The residue was dissolved in EtOAc and washed with 1N HCl, saturated $NaHCO_3$, and brine. The organic phase was dried ($MgSO_4$), filtered and the solvent removed to afford 21.3 g product. $^{13}$C NMR ($CDCl_3$) 16.66, 16.83, 20,01, 22.46, 23.41, 25.40, 40.11, 41.72, 43.75, 49.39, 51.37, 52.87, 56.42, 65.92, 77.39, 77.55, 77.81, 78.24, 127.42, 128.96, 129.19, 130.09, 137.41, 157.62, 169.00, 172.63, 173.24, 174.00.

Moc-Phe-Gly-Ala-Leucinol—Moc-Phe-Gly-Ala-Leu-OMe (21.3 g, 44.5 mmol) was dissolved in a mixture of 400 ml EtOH and 250 ml THF. The solution was cooled to 0° C. and 9.88 g (89.0 mmol) $CaCl_2$ was added. In 5 min the slurry had homogenized and 6.73 g (178.0 mmol) $NaBH_4$ added portionwise over a period of 5 min. The solution was stirred at 0° C. for 2 hours and the reaction carefully quenched with 1N HCl. The EtOH and THF were removed under vacuum and the remaining aqueous mixture extracted with 500 ml EtOAc. This organic phase was washed with saturated $NaHCO_3$, brine, and the organic phase dried with $MgSO_4$. Filtration and removal of solvent afforded 20.0 g of an off-white crystalline material. Chromatography on silica (3.5% $MeOH/CH_2Cl_2$) gave 13.0 g pure product. $R_f$=0.3 (10% $MeOH/CH_2Cl_2$). $^{13}C$ NMR ($CDCl_3$) 17.50, 22.23, 23.12, 24.84, 37.22, 39.76, 43.96, 49.88, 50.93, 52.48, 58.22, 65.27, 98.46, 98.54, 127.04, 128.68, 129.10, 136.62, 157.85, 170.71, 173.85, 174.45.

Moc-Phe-Gly-Ala-Leu-H (7)—29.9 g (70.7 mmol) of Dess-Martin periodinane was suspended in 500 ml $CH_2Cl_2$ and stirred for 10 min. Moc-Phe-Gly-Ala-Leucinol (10.6 g, 23.5 mmol) was dissolved in 100 ml $CH_2Cl_2$ and added at a moderate rate to the periodinane slurry. The mixture was stirred for 1 h and poured into 150 ml $NaHCO_3$ containing 123 g $Na_2S_2O_3$. The mixture was allowed to stir for 15 min and extracted with EtOAc. The organic phase was dried and filtered followed by removal of solvent. Chromatography (3.5% $MeOH/CH_2Cl_2$) on silica gave 5.1 g of pure white solid that is a mixture of the methoxy hemiacetal and aldehyde. $^{13}C$ NMR ($CDCl_3$, $CD_3OD$) 17.62, 17.94, 21.53, 21.71, 22.99, 23.30, 23.39, 24.54, 37.05, 37.70, 37.92, 38.24, 42.87, 49.83, 51.79, 52.14, 52.40, 56.75, 57.19, 98.40, 99.18, 127.00, 128.60, 129.06, 136.44, 157.27, 169.19, 169.67, 172.73, 173.40, 200.43.

Moc-Phe-OH (2)—L-Phenylalanine (5.0 g, 30.2 mmol) was dissolved in 30 ml 1N NaOH and cooled to 0° C. Methyl chloroformate (2.53 ml, 31.8 mmol) was added dropwise while in a separate addition funnel 30 ml of 1N NaOH was added simultaneously. After addition was complete the solution was washed with 200 ml EtOAc and the aqueous phase acidified to pH=2. The mixture was extracted with EtOAc (2X 100 ml), dried ($MgSO_4$), filtered, and the solvent removed to afford 6.0 g product. $^{13}C$ NMR ($CDCl_3$) 37.75, 52.57, 54.64, 128.63, 129.35, 135.74, 156.77, 175.76.

Mac-Phe-OH (9)—To a solution of 1.00 g (2.34 mmol) of Phe-OBn.PTSA in $Et_2O$ at room temperature was added 0.36 ml (2.57 mmol) of TEA. This was followed by the addition of 10 ml MeOH and then 0.14 ml (2.34 mmol) of methyl isocyanate in 4 ml $Et_2O$ was added dropwise. The reaction mixture was poured into 50 ml water and the phases separated. The organic phase was dried with $MgSO_4$, filtered and the solvent removed to give 0.66 g of product (96% yield). $^{13}C$ NMR ($CDCl_3$) 27.05, 38.47, 53.45, 54.64, 65.90, 127.43, 127.85, 128.48, 129.28, 130.27, 135.23, 136.22, 158.17, 173.08. To a solution of the crude product (2.11 mmol) in 25 ml MeOH was added 0.120 g Pd/C and the slurry degassed. The slurry was stirred under a positive pressure of $H_2$ via balloon for 1.5 h. The slurry was filtered through Celite and the filter cake washed with MeOH. The solvent was removed to afford 0.430 g product. $^{13}C$ NMR 26.50, 37.92, 54.28, 126.69, 128.28, 129.28, 136.65, 159.36, 175.33.

Mac-Phe-Gly-Ala-Leucinol (10)—To a solution of 0.200 g Mac-Phe-OH (0.900 mmol) and 0.253 g Gly-Ala-Leu-OMe.HCl (0.818 mmol, generated by hydrogenation of 5 according to the procedure outlined for compound 6) in 15 ml DMF was added 0.250 ml TEA (1.80 mmol) followed by the addition of 0.147 ml DECP (0.900 mmol). The mixture was stirred overnight and the solvent removed. The residue was redissolved in EtOAc and washed successively with 0.3N HCl, saturated $NaHCO_3$, and brine. The solution was dried, filtered and the solvent removed to give 0.300 g product. The crude product (0.628 mmol) is dissolved in 17 ml EtOH and cooled to 0° C. To this solution is added 0.140 g $CaCl_2$ (1.25 mmol) in 4 ml THF. To the resulting slurry is added 0.095 g $NaBH_4$ in one portion. After 45 min. the solution is quenched with water and extracted with EtOAc. The organic phase is dried with $MgSO_4$, filtered and the solvent removed. Chromatography with 4% $MeOH/CH_2Cl_2$ gave 0.200 g pure product. $^{13}C$ NMR ($CD_3OD$) 16.84, 21.05, 22.60, 24.51, 25.66, 37.41, 39.73, 42.67, 49.65, 56.63, 64.33, 126.63, 128.32, 128.96, 137.12, 160.01, 170.45, 173.60, 175.03.

Mac-Phe-Gly-Ala-Leu-H (11)—To a slurry of Dess-Martin periodinane (0.565 g, 1.33 mmol) in 15 ml $CH_2Cl_2$ was added a suspension of Mac-Phe-Gly-Ala-Leucinol (0.200 g, 0.445 mmol) in $CH_2Cl_2$ and the resulting slurry stirred for 0.5 h. The mixture was poured into saturated $NaHCO_3$ containing 2.32 g $Na_2S_2O_3$ and the solution stirred for 10 min., followed by extraction with EtOAc. The organic phase is dried with $MgSO_4$, filtered and the solvent removed. The residue is chromatographed on silica to give 0.081 g product. $^{13}C$ NMR (10% $CD_3OD$ in $CDCl_3$) 17.18, 17.43, 21.35, 21.55, 23.26, 23.34, 24.40, 24.47, 26.36, 26.60, 37.25, 37.38, 38.60, 42.86, 42.97, 51.77, 51.93, 54.94, 56.75, 57.00, 98.7, 99.32, 126.87, 128.49, 128.91, 136.51, 159.53, 159.55, 169.93, 170.39, 173.63, 173.85, 174.70.

Z=carbobenzyloxy
Gly=glycine
Ala=alanine
Leu=leucine
Phe=phenylalanine
OMe=methyl ester
TEA=triethylamine
DECP=diethylcyanophosphonate
TLC=thin layer chromatography
MeOH=methanol
Pd/C=palladium on activated carbon
EtOH=ethanol
THF=tetrahydrofuran
Mac=methylaminocarbonyl Scheme A
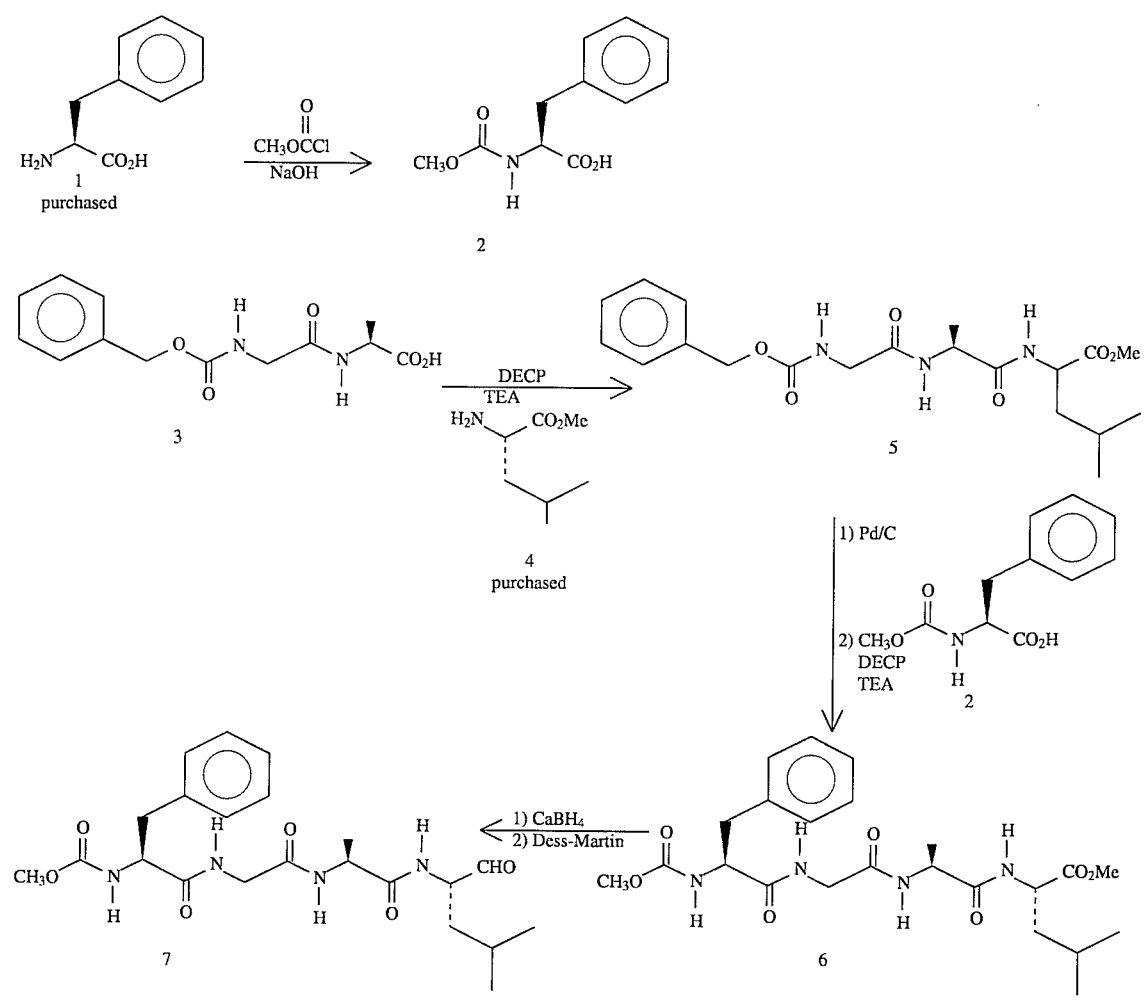

Scheme B

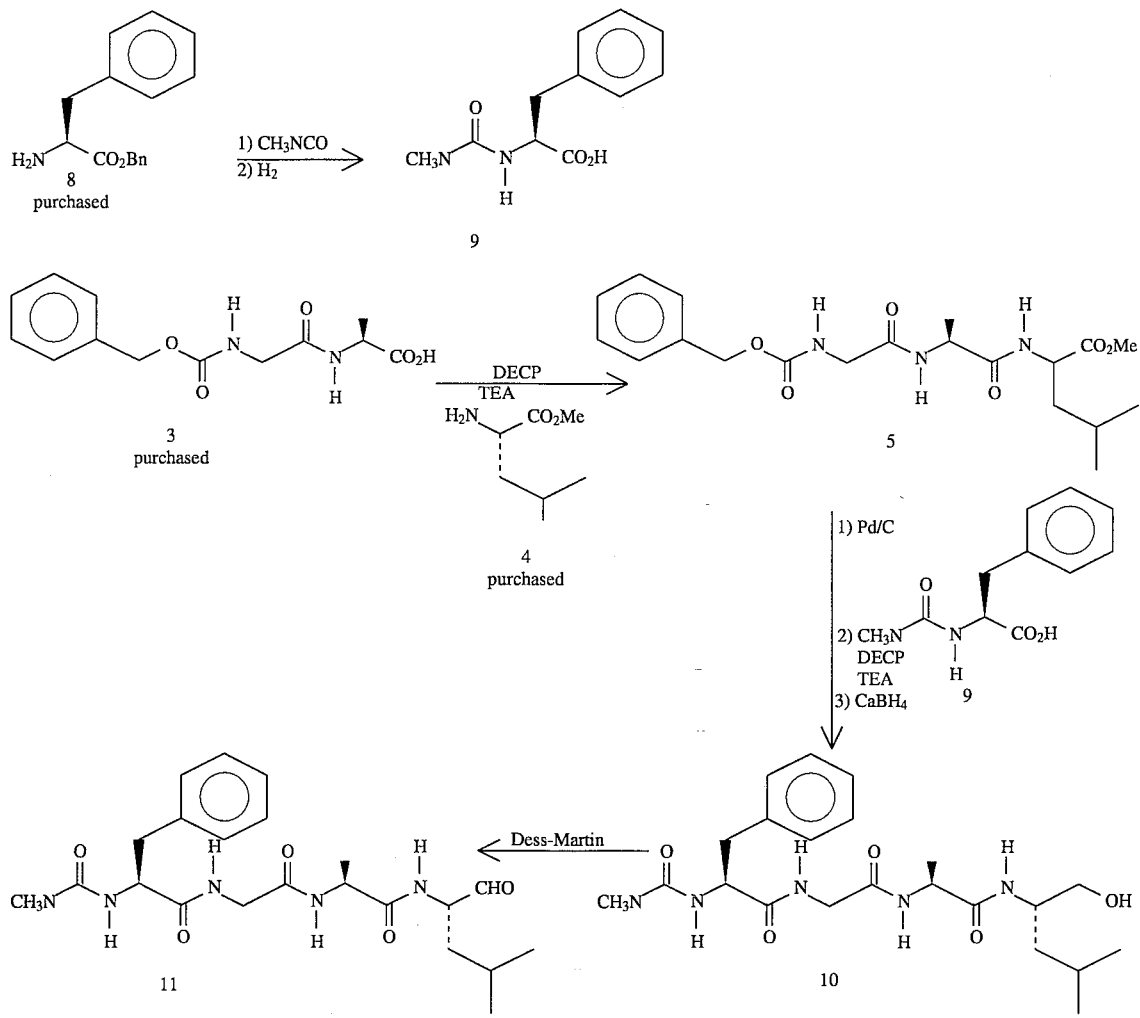

What is claimed is:

1. A liquid aqueous detergent composition comprising:
   (a) from 1% to 80% of a detersive surfactant;
   (b) from 0.0001% to 1.0% of active proteolytic enzyme or mixtures thereof; and
   (c) from 0.00001% to 5% of a peptide aldehyde comprising 2–3 amino acids with a C terminal end aldehyde of an amino acid and the N-terminal end protected by a carbamate or an urea group.

2. The liquid aqueous detergent composition according to claim 1 wherein the peptide aldehyde is selected from aldehydes having 3 amino acids wherein the C terminal end is selected from Ala-LeuH and Ala-PheH.

3. The liquid aqueous detergent composition according to claim 2 wherein the peptide aldehyde is selected from the group consisting of Phe-Gly-Ala-LeuH, Phe-Gly-Ala-PheH, having a N-terminal end protected carbamate or urea thereof.

4. The liquid aqueous detergent composition according to claim 1 wherein the proteolytic enzyme is selected from subtilisin-type protease.

5. The liquid aqueous detergent composition according to claim 2 wherein the proteolytic enzyme is selected from subtilisin-type protease.

6. The liquid aqueous detergent composition according to claim 3 wherein the proteolytic enzyme is selected from subtilisin-type protease.

* * * * *